United States Patent [19]

Derrien et al.

[11] Patent Number: 4,463,206
[45] Date of Patent: Jul. 31, 1984

[54] PROCESS FOR PRODUCING BENZENE BY HYDRODEALKYLATION OF A HYDROCARBON FRACTION COMPRISING ALKYL-AROMATIC HYDROCARBONS, OLEFINIC HYDROCARBONS AND SULFUR COMPOUNDS

[75] Inventors: Michel Derrien, Rueil Malmaison; Jean Cosyns, Maule, both of France

[73] Assignee: Institut Francais du Petrole, Rueil-Malmaison, France

[21] Appl. No.: 456,462

[22] Filed: Jan. 7, 1983

[30] Foreign Application Priority Data

Jan. 7, 1982 [FR] France ............................... 82 00273

[51] Int. Cl.$^3$ ............................................. C07C 4/12
[52] U.S. Cl. ................................... 585/483; 585/251; 208/319
[58] Field of Search ...................... 585/251, 319, 483; 208/89, 97, 57

[56] References Cited

U.S. PATENT DOCUMENTS

| 3,222,410 | 12/1965 | Swanson | 585/252 |
| 3,310,592 | 3/1967 | Fukuda et al. | 208/57 |
| 3,625,879 | 12/1971 | Horne et al. | 585/251 |
| 3,720,729 | 3/1973 | Sze et al. | 585/251 |
| 3,844,734 | 10/1974 | Johnson | 208/97 |

FOREIGN PATENT DOCUMENTS

| 1120022 | 7/1968 | United Kingdom | 585/319 |
| 1147706 | 4/1969 | United Kingdom | 585/319 |

Primary Examiner—Delbert E. Gantz
Assistant Examiner—Cynthia A. Prezlock
Attorney, Agent, or Firm—Millen & White

[57] ABSTRACT

A stabilized hydrocarbon fraction comprising toluene, xylene, sulfur and olefinic hydrocarbons is converted to benzene by (a) catalytic hydrodesulfuration, (b) hydrodealkylation and (c) catalytic hydrogenation.

8 Claims, No Drawings

PROCESS FOR PRODUCING BENZENE BY HYDRODEALKYLATION OF A HYDROCARBON FRACTION COMPRISING ALKYL-AROMATIC HYDROCARBONS, OLEFINIC HYDROCARBONS AND SULFUR COMPOUNDS

BACKGROUND OF THE INVENTION

This invention relates to the production of benzene from a stabilized hydrocarbon fraction comprising alkylaromatic hydrocarbons, unsaturated hydrocarbons and sulfur compounds.

A known method for producing benzene from a stabilized hydrocarbons fraction, i.e. a fraction made free of the components of lower stability (diolefins and acetylenics), consists of subjecting this fraction to catalytic hydrodesulfuration, followed with hydrodealkylation. The unconverted $C_7$ and $C_8$ hydrocarbons may be recycled. When the hydrocarbon charge has a low sulfur content, for example less than 100 ppm by weight (b.w.) no serious difficulty is encountered. Conversely, when the hydrocarbon charge has a higher sulfur content, for example more than 100 ppm b.w., the catalytic hydrodesulfuration which converts the organic sulfur compounds mainly to $H_2S$ must be followed with cooling and condensation of the hydrocarbon fraction, so as to separate it from a gas phase containing hydrogen sulfide. As a matter of fact, the presence of $H_2S$ in substantial amounts in the hydrodealkylation step results in the formation of thiophene which cannot be separated easily from benzene. The resultant benzene does not comply with the specifications of industry (a maximum of 1 ppm b.w. of thiophene).

The fractionation destined to eliminate $H_2S$ before hydrodealkylation is costly as concerns investment and energy since the hydrodesulfuration effluent must be cooled and then reheated to the elevated hydrodealkylation temperature.

According to U.S. Pat. No. 3,222,410 and U.S. Pat. No. 3,310,592, stabilized gasoline is subjected to hydrodealkylation followed with hydrodesulfuration of benzene. This process is not adapted to extended hydrodealkylation periods, since coal-like particles separate, and the benzene yield is poor, as unconverted toluene and xylenes cannot be recycled to the hydrodealkylation step, due to their content of thiophane and other sulfur compounds.

SUMMARY OF THE INVENTION

The invention meets the above difficulties as follows:

(a) a stabilized hydrocarbon fraction comprising toluene and/or xylene, admixed with a recycle stream from subsequent step (e), is subjected to catalytic hydrodesulfuration, so as to decrease by at least 90% (preferably at least 99%) the sulfur content of said fraction and to decrease the mono-olefin content so that the bromine number of the resultant fraction is at most 2 (mg $Br_2/100$ g), and preferably lower than 0.5, (b) the products of step (a) are directly supplied to a hydrodealkylation step, without $H_2S$ removal, (c) the hydrodealkylation product is directly subjected (without $H_2S$ removal) to a catalytic hydrogenation step whose main purpose is to remove thiophene by hydrogenation, (d) the hydrogenation products are fractionated so as to recover a benzene fraction and a fraction comprising toluene and/or xylene, (e) the fraction comprising toluene and/or xylene is recycled to step (a) where it constitutes said recycle stream.

DETAILED DISCUSSION

Two embodiments of step (c) can be selected:

use of a conventional hydrodesulfuration catalyst (at least one compound of the following metals: Co, Ni, Mo, W): the extent of the desulfuration is slightly greater, but a substantial amount of cyclohexane is formed; it is however not a disadvantage when benzene is destined to be hydrogenated thereafter to cyclohexane.

use of a palladium containing catalyst: the formation of cyclohexane is negligible, which increases the benzene yield; and the removal of thiophene complies with the industrial specifications (at most 1 ppm b.w. of thiophene).

In addition to palladium, the catalyst may contain other metals, for example silver and gold.

The processed hydrocarbon charge is a stabilized hydrocarbon fraction comprising toluene and/or xylene, as well as benzene and/or other $C_8$ or $C_9$ alkylaromatic hydrocarbons. It also contains saturated and mono-olefinic hydrocarbons. Examples of these alkylaromatic hydrocarbon fractions are the fractions: $C_7$ $C_8$; $C_6$ $C_7$; $C_6$ $C_7$ $C_8$; $C_6$ $C_7$ $C_8$ $C_9$; $C_7$ $C_8$ $C_9$ or $C_8$ $C_9$.

A "stabilized" fraction is defined as a hydrocarbon fraction substantially free of acetylenic and diolefinic hydrocarbons; it is specially the case of a steam-cracking gasoline fraction which has been subjected to selective hydrogenation to remove at least the major part of the acetylenic and diolefinic hydrocarbons without excessive hydrogenation of the mono-olefinic hydrocarbons and without substantial desulfuration. This well-known type of treatment is effected in contact with a catalyst belonging to at least one of the groups VI and VIII (noble and non-noble metals) at a temperature lower than about 230° C.

The stabilized hydrocarbon charge normally has a M A V (maleic anhydride value) lower than 4 (mg of maleic anhydride per gram) and a sulfur content of at least 100 ppm b.w. Its bromine number (g $Br_2/100$ g) is normally higher than 5.

The hydrodesulfuration is effected under conventional conditions, i.e. in contact with a conventional hydrodesulfuration catalyst comprising at least one molybdenum, tungsten, cobalt and/or nickel compound, for example a supported cobalt-molybdenum, nickel-molybdenum or nickel-tungsten catalyst.

The carrier is, for example, alumina.

These catalysts are well known and a detailed description thereof is thus unnecessary.

The hydrodesulfuration conditions are usually: a temperature of 250° to 400° C., preferably 300° to 350° C., a pressure of 10 to 150 bars, preferably 20 to 50 bars, a liquid hydrocarbon feed rate (L. H. S. V.) of 0.1 to 10 liters, preferably 1 to 4 liters per liter of catalyst per hour and a hydrogen feed rate of 0.5 to 10 moles per mole of the hydrocarbon liquid charge.

The crude hydrodesulfuration product, comprising the desulfurized hydrocarbons and the formed hydrogen sulfide, is subjected without fractionation to hydrodealkylation. Hydrogen may be added when the amount not consumed in the hydrodesulfuration step for sulfur removal and olefin hydrogenation is insufficient.

The hydrodealkylation may be effected under conventional conditions, i.e. a temperature of 600° to 800° C., preferably 650° to 730° C., and a pressure of 5 to 70 bars, preferably 20 to 50 bars. The hydrogen proportion is, for example, 1 to 20 moles of hydrogen per mole of hydrocarbons.

The residence time, determined for the overall reaction mixture (hydrocarbons+hydrogen) is, for example, from 5 seconds to 2 minutes.

A conventional hydrodealkylation catalyst can be used; however a catalyst is not necessary in this step, and the absence of catalyst is even preferred.

The hydrodealkylation reaction can be continued over long periods without detrimental coke deposit, as a result of two factors: the absence of olefins (they have been hydrogenated in the hydrodesulfuration step) and the presence of hydrogen sulfide (formed in the hydrodesulfuration step).

In the course of the hydrodealkylation reaction, the alkylaromatic hydrocarbons are converted to benzene and the non-aromatic hydrocarbons are hydrocracked to lower hydrocarbons such as methane and ethane.

After the hydrodealkylation step, the content of organic sulfur compounds, particularly of thiophene, has increased up to levels incompatible with industrial standards. Hydrogenation is then performed with the main purpose of converting thiophene, which is not easily separable from benzene, to more easily separable sulfur compounds.

This hydrogenation is effected under conditions which do not substantially differ from the general conditions disclosed above for hydrodesulfuration. However, as indicated above, two types of catalysts may be used: a catalyst containing palladium or a catalyst of non-noble metal containing at least one metal or a compound of a metal selected from the following: Co, Ni, Mo, W with the above advantages and disadvantages, for example a catalyst containing both cobalt and molybdenum.

The crude product of this hydrogenation is nearly free of thiophene. Sulfur can be found therein as $H_2S$, thiophene and various sulfides or thiols which can be easily separated from benzene: a large proportion of these sulfur compounds can be found in the alkylaromatic hydrocarbons fraction (toluene and possibly xylenes and other alkylaromatic hydrocarbons, including tetrahydronaphthalene) which are recycled to the hydrodesulfuration step constituting the first step of the process. This recycling of organic sulfur compounds is not detrimental since these compounds are eliminated in the hydrodesulfuration step, essentially by conversion to $H_2S$.

The crude hydrogenation product may thus be easily fractionated to gaseous components ($H_2$, $H_2S$, light hydrocarbons boiling below benzene), to benzene of high purity an alkylaromatic hydrocarbons fraction, at least a part of which is recycled to the hydrodesulfuration step.

EXAMPLE 1

The feed charge is a $C_6$-$C_9$ steam-cracking fraction previously selectively hydrogenated (stabilized) to remove the acetylenic and diolefinic hydrocarbons.

The analysis of the stabilized charge is the following:

| | |
|---|---|
| paraffins and cycloparaffins (% b.w.) | 8.85 |
| olefins and cycloolefins | 7.90 |
| benzene | 34.70 |
| toluene | 18.95 |
| $C_8$ + $C_9$ alkylaromatics | 29.60 |
| | 100.00 |
| Bromine number (g $Br_2$/100 g) | 15 |
| total sulfur, ppm by weight | 500 |
| thiophene and homologs, ppm by weight (ASTM D 1685-T) | 1180 |
| Maleic anhydride value (mg/g) | 1 |

This charge is admixed with hydrogen and the recycled $C_7$-$C_{10}$ alkylaromatic fraction which will be mentioned later, in a proportion of 10.6 parts b.w. of the recycled $C_7$-$C_{10}$ fraction for 100 parts b.w. of the $C_6$-$C_9$ fraction.

The resultant mixture is contacted with a catalyst of 2.5% b.w. CoO and 14% b.w. $MoO_3$ on alumina. The conditions are the following:
T=320° C.; P=35 bars; LHSV=2; $H_2$/HC=2.5 mole/mole.

After completion of the hydrodesulfuration, the bromine number is 0.1, the sulfur content 0.5 ppm by weight and the acid wash color 1 (D 848-29).

The hydrodesulfuration effluent is fed without fractionation to the hydrodealkylation step.

Operating conditions of the thermal hydrodealkylation: T=705° C.; P=25 bars; residence time ($H_2$+hydrocarbons)=30 sec; $H_2$/HC molar ratio=5.

The proportion of benzene in the hydrodealkylation product is 83% b.w. with respect to the total hydrocarbons.

The organic sulfur content is 7 ppm by weight (thiophene content: 4 ppm b.w.) and the acid wash color is 9, as a result of the formation of traces of diolefins and olefins.

The hydrodealkylation effluent is supplied without fractionation to a hydrogenation reactor whose catalyst consists of 0.3% Pd on alumina. Operating conditions: T=315° C., P=43 bars, LHSV=5, $H_2$/HC=1 mole/mole.

The hydrogenation product is fractionated to:
gaseous components and hydrocarbons up to $C_5$.
benzene fraction. Yield 91.7% b.w. with respect to the aromatics of the initial $C_6$-$C_9$ charge.

| | |
|---|---|
| Cyclohexane content | 0.06% b.w. (by gas chromatography) |
| Acid wash color | 1 (D 848 - 29) |
| Total sulfur | 4 ppm by weight (D 1320) |
| Thiophene | 0.4 ppm by weight (D 1685 - T) |

It must be emphasized that the excellent acid wash color has been obtained without the clay treatment conventionally effected after a hydrodealkylation.

$C_7$-$C_{10}$ alkylaromatic fraction which is recycled to hydrodesulfuration.

COMPARISON EXAMPLE

Example 1 is repeated, except that the $C_7$-$C_9$ fraction is not recycled; the benzene yield is only 82.3% b.w. Benzene purity is unaffected.

EXAMPLE 2

The operation is the same as in Example 1, except that the catalyst used for hydrogenation, instead of being based on palladium, consists of CoO: 2.5% b.w., $MoO_3$: 14% b.w. on alumina.

The hydrogenation operating conditions are unchanged.

The benzene fraction is obtained with a yield of 91.9% but the cyclohexane content of this benzene fraction is 3% b.w., which shows that the catalyst of this example is not so satisfactory as the palladium catalyst of Example 1.

What is claimed is:

1. A process for producing benzene from a stabilized hydrocarbon fraction comprising toluene, xylene or a mixture thereof, sulfur and olefinic hydrocarbons, and having a sulfur content of at least 100 ppm by weight, a bromine number higher than 5, and a maleic anhydride value lower than 4, said process comprising the steps of:
    (a) contacting a mixture of said stabilized hydrocarbon fraction and a recycle hydrocarbon fraction from step (e), in the presence of hydrogen, with a hydrodesulfuration catalyst, under hydrodesulfuration conditions comprising a temperature of 250°–400° C. and a pressure of 10–150 bars, so selected as to reduce by at least 90% the sulfur content of said mixture, and to reduce its monoolefin content to such an extent that the bromine number of the resultant effluent is at most 2;
    (b) subjecting the unfractionated crude hydrodesulfuration product, containing H$_2$S, to hydrodealkylation conditions comprising a temperature of 600°–800° C. and a pressure of 5–70 bars;
    (c) subjecting the unfractionated hydrodealkylation product to catalytic hydrogenation, at a temperature of 250°–400° C., under a pressure of 10–150 bars, whereby thiophene is converted to other sulfur compounds;
    (d) fractionating the catalytic hydrogenation effluent, and separately recovering a gaseous fraction, a product benzene fraction, and a fraction comprising toluene, xylene or a mixture thereof, and containing sulfur, and
    (e) recycling at least a portion of said sulfur-containing fraction comprising toluene, xylene or a mixture thereof to step (a).

2. A process according to claim 1, wherein the catalyst of step (c) comprises palladium.

3. A process according to claim 1, wherein step (a) is effected under such conditions that the sulfur content of said mixture is reduced by at least 99% and the bromine number thereof is reduced to a value of at most 0.5.

4. A process according to claim 1, wherein said stabilized hydrocarbon fraction is a steam-cracking gasoline fraction previously subjected to selective hydrogenation to eliminate the acetylenic and diolefinic hydrocarbons.

5. A process according to claim 1, wherein the temperature of steps (a) and (c) is 300° to 350° C. and the pressure is 20 to 50 bars.

6. A process according to claim 1, wherein in step (b), the temperature is 650°–730° C., and the pressure is 20–50 bars.

7. A process according to claim 1, wherein in step (b) the amount of hydrogen is 1–20 moles per mole of hydrocarbons.

8. A process according to claim 1, wherein the residence time of the total reaction mixture in step (b) is 5 seconds to 2 minutes.

* * * * *